United States Patent
Vitiello et al.

(10) Patent No.: US 9,814,605 B2
(45) Date of Patent: Nov. 14, 2017

(54) COMBINATION PROSTHETIC AND ORTHOTIC DEVICE

(71) Applicant: SCUOLA SUPERIORE DI STUDI UNIVERSITARI E DI PERFEZIONAMENTO SANT'ANNA, Pisa (IT)

(72) Inventors: Nicola Vitiello, Pontedera (Pisa) (IT); Tommaso Lenzi, Massa a Cozzile (Pistoia) (IT); Stefano Marco Maria De Rossi, Mirano (Venezia) (IT); Francesco Giovacchini, Pisa (IT); Marco Cempini, Terricciola (Pisa) (IT); Maria Chiara Carrozza, Pisa (IT)

(73) Assignee: SCUOLA SUPERIORE DI STUDI UNIVERSITARI E DI PERFEZIONAMENTO SANT'ANNA, Pisa (IT)

( * ) Notice: Subject to any disclaimer, the term of this patent is extended or adjusted under 35 U.S.C. 154(b) by 66 days.

(21) Appl. No.: 14/409,465

(22) PCT Filed: Jun. 20, 2013

(86) PCT No.: PCT/IB2013/055065
§ 371 (c)(1),
(2) Date: Dec. 18, 2014

(87) PCT Pub. No.: WO2013/190495
PCT Pub. Date: Dec. 27, 2013

(65) Prior Publication Data
US 2015/0190248 A1    Jul. 9, 2015

(30) Foreign Application Priority Data
Jun. 21, 2012   (IT) .................................. FI2012A0129

(51) Int. Cl.
*B25J 9/00* (2006.01)
*A61F 5/01* (2006.01)
(Continued)

(52) U.S. Cl.
CPC .................. *A61F 2/70* (2013.01); *A61F 2/60* (2013.01); *A61F 2/605* (2013.01); *A61F 5/0102* (2013.01);
(Continued)

(58) Field of Classification Search
CPC .... A61F 2/50; A61F 2/60; A61F 2/601; A61F 2/602; A61F 2/604; A61F 2/605;
(Continued)

(56) References Cited

U.S. PATENT DOCUMENTS 406,328 A * 7/1889 Yagn ...................... A63B 25/10
                                                    297/4
3,995,324 A   12/1976 Burch
(Continued)

OTHER PUBLICATIONS

Datta D., Heller et al. A comparative evaluation of oxygen consumption and gait pattern in amputees using Intelligent Prostheses and conventionally damped knee swing-phase control. Clin Rehabil, 19:pp. 398-403. (2005).
(Continued)

*Primary Examiner* — Thomas J Sweet
*Assistant Examiner* — Christie Bahena
(74) *Attorney, Agent, or Firm* — Steinfl + Bruno LLP

(57) ABSTRACT

An aid device for the motor disabled, suitable for allowing walking of transfemoral amputees, having: a lower-limb prosthesis of an amputated limb; a lower-limb orthosis suitable to be worn at a sound contralateral lower-limb; an orthotic pelvis module connecting the prosthesis to the
(Continued)

lower-limb orthosis; and a control unit for the operational coordination of movements of the prosthesis and the lower-limb orthosis.

15 Claims, 3 Drawing Sheets

(51) Int. Cl.

| | |
|---|---|
| *A61F 2/60* | (2006.01) |
| *A61F 2/68* | (2006.01) |
| *A61F 2/70* | (2006.01) |
| *A61F 2/76* | (2006.01) |
| *A61F 2/54* | (2006.01) |
| *A61F 2/64* | (2006.01) |
| *A61F 2/66* | (2006.01) |

(52) U.S. Cl.
CPC .............. *B25J 9/0006* (2013.01); *A61F 2/54* (2013.01); *A61F 2/64* (2013.01); *A61F 2/66* (2013.01); *A61F 2/68* (2013.01); *A61F 2002/6827* (2013.01); *A61F 2002/701* (2013.01); *A61F 2002/704* (2013.01); *A61F 2002/764* (2013.01); *A61F 2002/7615* (2013.01); *A61F 2002/7625* (2013.01); *A61F 2002/7635* (2013.01); *A61F 2002/7645* (2013.01); *F04C 2270/0421* (2013.01)

(58) Field of Classification Search
CPC ...... A61F 2/64; A61F 2/68; A61F 2/76; A61F 5/0193; A61F 2002/7865; A61F 2002/607; A61F 2002/608; B25J 9/0006
See application file for complete search history.

(56) References Cited

U.S. PATENT DOCUMENTS

| | | | |
|---|---|---|---|
| 2005/0059908 A1* | 3/2005 | Bogert | A61F 5/0102 601/5 |
| 2007/0056592 A1* | 3/2007 | Angold | A61H 3/00 128/845 |
| 2010/0268351 A1* | 10/2010 | van der Merwe | G05B 15/02 623/24 |
| 2012/0109013 A1* | 5/2012 | Everett | A61B 5/1036 600/587 |
| 2015/0001269 A1* | 1/2015 | Sacksteder | F16M 13/04 224/576 |

OTHER PUBLICATIONS

Dillingham T.R. et al. Limb amputation and limb deficiency: epidemiology and recent trends in the United States. South Med J., 95(8):875-883. (2002).

Ephraim P.L., et al. Epidemiology of limb loss and congenital limb deficiency: A review of the literature. Archives of Physical Medicine and Rehabilitation, 84(5): pp. 747-761 (2003).

The Global Lower Extremity Amputation Study Group Epidemiology of lower extremity amputation in centres in Europe, North America and East Asia. British Journal of Surgery, 87: pp. 328-337. (2000).

Waters R.L., et al. Energy cost of walking of amputees: the influence of level of amputation. The Journal of Bone and Joint Surgery, 58(1): pp. 42-46 (1976).

PCT International Search Report mailed on Feb. 18, 2014 for PCT/IB2013/055065 dated Jun. 20, 2013 in the name of Scuola Superiore Di Studi Universitari E Di Perfezionamento Sant'Anna.

PCT Written Opinion dated Feb. 18, 2014 for PCT/162013/055065 filed on Jun. 20, 2013 in the name of Scuola Superiore Di Studi Universitari E Di Perfezionamento Sant'Anna.

* cited by examiner

FIG. 1
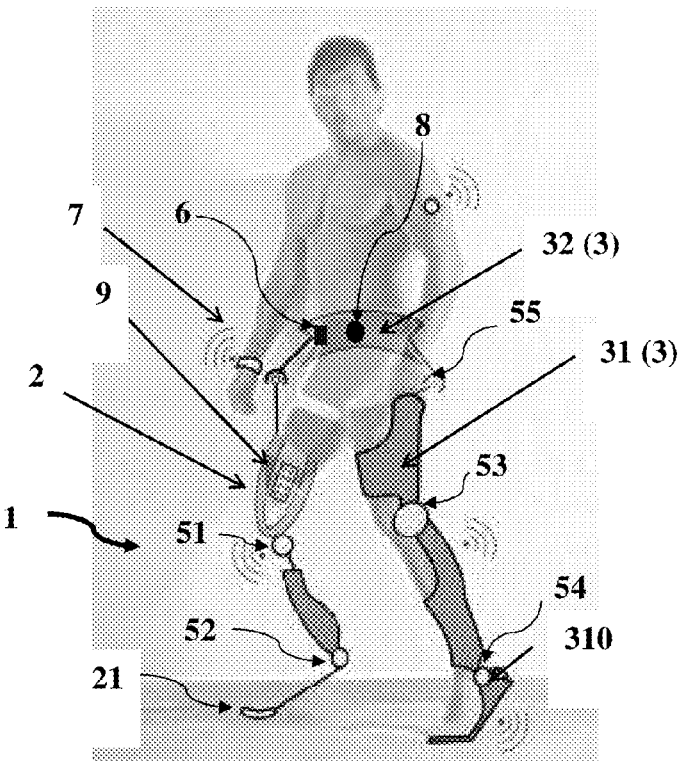
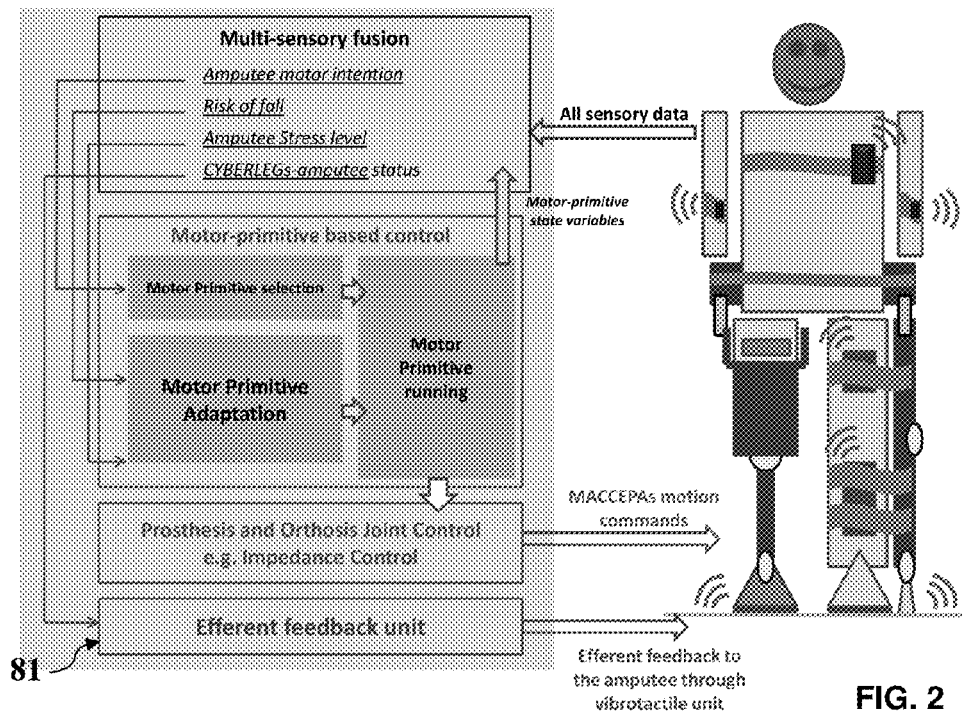
FIG. 2

COMBINATION PROSTHETIC AND ORTHOTIC DEVICE

CROSS REFERENCE TO RELATED APPLICATIONS

The present application is the US national stage of International Patent Application PCT/IB2013/055065 filed internationally on Jun. 20, 2013 which, in turn, claims priority to Italian Patent Application No. FI2012A000129 filed on Jun. 21, 2012.

Field of the Invention

The present invention relates to an aid device for the motor disabled, particularly suitable for lower leg amputees.

The work leading to this invention has received funding from the European Union Seventh Framework Programme FP7/2007-2013, within the framework of the CYBERLEGs Project, grant agreement n° 287894.

Background of the Invention

Lower-limb loss is a potentially disabling condition affecting the health and well-being of persons worldwide.

Across the globe, lower-limb loss has been acknowledged as a significant public health issue, and strategies have been developed to reduce the burden of disease (Ephraim, Dillingham, Sector, Pezzin & MacKenzie, 2003). To better quantify the incidence of lower-limb amputations and have a dimension of the problem, we should realize that every year—only in US—about 150,000 people undertake a lower-limb amputation caused by a vascular disease (http://www.amputee-coalition.org).

There are multiple pathways to the loss of a limb, including diabetes mellitus, peripheral vascular disease, trauma, malignancy, and congenital limb deficiency. Universal to all developed countries there are two main factors influencing the amount of lower-limb amputations. The first factor is peripheral vascular disease, which is in most of the cases caused by diabetes mellitus (amputations caused by a vascular disease are called dysvascular). It is estimated that, in US, 80% of all lower-limb amputations are dysvascular, while those caused by trauma are about 15% (other causes are cancer or congenital diseases). The second factor is the age-related increase of low-extremity amputations secondary to peripheral vascular disease, with over-70 people being the ones having the highest risk of undertaking dysvascular amputation (Dillingham, Pezzin, & MacKenzie, 2002; Ephraim et al. 2003; The Global Lower Extremity Amputation Study Group, 2000). This latter aspect is a critical point if we consider that ageing is one of the future social challenges for Europe. In fact, in 40 years from now, nearly 35% of the population of Europe is projected to be 60 years of age or over and we should consider now how to evolve towards a society where this part of the population will remain creative, productive, autonomous, and independent.

Lower-limb amputation can be performed at several levels (e.g. foot-level, calf-level, thigh-level). Although all amputations lead to a disabling condition for the patient, thigh-level amputations (namely transfemoral) are clearly the most challenging amputation level for the amputee, the surgeon, prosthetists, therapists, and every member of the healthcare staff. Transfemoral amputees are estimated to be about the 20% of the total lower-limb amputations, this means about 30,000 per year, only in US (Dillingham et al., 2002). In Europe data are very similar.

Drawbacks Associated with the Use of Prior Art Prostheses
Transfemoral Amputation is a Big Challenge for the Amputee's Daily Life.

In fact, persons living with transfemoral limb loss face multiple distinct challenges, namely: (i) they need more metabolic energy and cognitive effort to perform any locomotion-related task (e.g. gait, climbing stairs), (ii) their locomotion is less stable, (iii) they need a more complicated prosthetic device, (iv) they face a tremendous difficulty rising from a seated position, and (v) differently from amputees with amputations at the tibia and the foot, they lack prosthetic comfort while sitting.

Generally speaking, transfemoral amputees using a prosthesis require more energy to walk, at the same time achieving lower speeds than non-amputees.

No lower-limb amputation is "easy" to adapt to, but the transfemoral certainly offers more challenges than amputations in the calf or foot. Studies show that the higher the amputation level, the more energy is needed for walking. A famous study of Waters et al. (1976) looked at gait and energy use among 70 people with lower-limb amputations at several levels. In this study it was shown that transfemoral amputees choose the slowest gait speed (about 60% of the one of non-amputees), and consume 1.3 times the energy that non-amputees consume for walking the same distance. These values become even worse in the case of dysvascular amputees: about 40% of the non-amputee gait speed and 2.5 times the energy that non-amputee expend. In other terms, a person with a dysvascular transfemoral amputation usually walks more slowly than before but expends much more energy because it takes a greater effort to walk after amputation.

Steps Stairs and Other Ups & Downs are Particularly Challenging Tasks.

People with transfemoral limb loss do not go "step over step" as they walk up or down stairs. Rather, they tend to go "step by step", one stair at a time. Typically, an individual with transfemoral limb loss will first step up with the sound leg (i.e. the contralateral leg), then bring the prosthetic side up to the same step. In this case the contralateral sound leg become fundamental to accomplish the desired motion task. This is because the passive prosthetic knee does not provide the power necessary to take the person up to the next higher step. Loss of knee and ankle torque is one of the factors that rises the challenge to adjust to a new way of walking after a transfemoral amputation.

In general terms, more "mental energy" is required from amputees, although less gait stability is achieved.

Transfemoral amputees face more problems with stumbling and falling, and much greater concentration is needed for walking. While traditional research such as the aforementioned Waters' work looked at the physical energy required for walking, newer research is trying to measure the mental energy involved (Datta & Howitt, 2005), namely:

"the conscious effort of thinking about walking and moving with the prosthesis";

"the stumbling", which is a "near miss" and does not systematically imply a fall; it corresponds to a stop or a change in the rhythm of the walk: recovery from stumble often requires a "stutter step", a hop or a shift in weight balance;

"the semi controlled fall", which occurs when the amputee recognizes the incipient fall, and as it occurs he/she grab onto something to either break the fall or land in a controlled manner;

and finally, the "uncontrolled fall", which is very risky for amputee health (http://www.amputee-coalition.org).

While stumbling and falling are clearly issues for all lower-limb amputees, the higher the amputation level, the greater the risks of falling. Walking is automatic for most individuals, with almost no conscious thought. A person with a transfemoral amputation, on the other hand, must really focus on walking, especially on uneven surfaces, stairs and inclines, and in unfamiliar areas. Different environments can bring different and sometimes hazardous challenges. It's one thing to take a leisurely walk on an even, smooth pathway, but it's something else altogether to navigate an area such as an airport concourse where people are walking at many speeds, stopping and starting, and coming in and out of "your space" from all directions. It is in this case that the amputee has to make countless gait.

As a consequence of all said challenges, energetic, cognitive and stability difficulties are not fully overcome by any artificial passive or active transfemoral prosthesis in the current state of the art. The consequence is that most of dysvascular transfemoral amputees (who are the more affected by these issues) do not use any prosthesis.

A few amputees (about 20%) use the prosthesis to walk or move. Rather they use alternative biomedical means such as wheelchairs. In many cases the medical doctors prohibit the use of the prosthesis because the reduced energy-efficiency of the resulting gait would be not sustainable by the weak cardiovascular system of the dysvascular amputee. Indeed, the presence of the passive prosthesis yields to a demanding additional load on the contralateral limb, which is often also impaired and affected by the same peripheral vascular disease.

The prosthesis requires the amputee to re-learn how to walk, by adapting his/her physiological gait pattern to the capabilities of the prosthesis. Some of these issues have been tackled by state-of-the-art semi-active or active prostheses. The first are like conventional passive prostheses, augmented with an active knee brake, the latter being real active devices that can provide positive power to the gait, reducing the burden on the user, and ensuring a more "physiological" pattern. Unfortunately, both active and semi-active prostheses are mostly used by young, healthy trauma amputees, while are still unusable for dysvascular amputees. Indeed, they unacceptably load the contralateral limb and are then extremely energy-inefficient for the amputee.

U.S. Pat. No. 3,995,324 discloses a passive device for moving the artificial leg of an amputee. The device includes a first articulated hip joint assembly carried at the natural leg and a second articulated hip joint assembly carried by the prosthesis. Energy from the movement of the natural leg is transferred to the movement of the artificial leg.

SUMMARY OF THE INVENTION

The technical problem underlying the present invention is therefore to overcome the drawbacks mentioned above with reference to the state of the art.

The above problem is solved by an aid device according to claim 1 and by a method according to claim 23.

In particular, in its most general definition the invention provides an aid device comprising a prosthesis of an amputated limb and an orthosis, the latter suitable to be worn at another body portion and preferably powered/motorized. The prosthesis and the orthosis are operatively connected and jointly controlled. Preferably, the orthosis comprises a first limb module to be worn at a (sound) limb contralateral to the amputated one and a second connection module for connecting the first module to the prosthesis.

For "operatively connected" it is meant that the prosthesis and the orthosis can be mechanically/structurally connected one to the other and/or functionally connected, in this latter case being controlled, typically electronically, by a common control unit.

The proposed combination of a prosthesis with an orthosis can be named "ortho-prosthesis". Such ortho-prosthesis is conceived as a complex "wearable" robotic device which acts and cooperates closely to a human being.

Further preferred features of the invention are indicated in the dependent claims.

In particular, in a preferred embodiment the prosthesis is a lower-limb prosthesis and the orthosis comprises a first module being a lower-limb orthosis and a second module being a pelvis module connecting the lower-limb prosthesis and the lower-limb orthosis.

Similarly, according to another preferred embodiment the prosthesis and the first orthosis module are wearable at an amputated upper limb and at a contralateral (sound) upper limb, respectively, and the second orthosis module is apt to be worn at the back of the subject.

The aid device according to the invention implements a novel concept of a technological biomedical aid which allows amputees, particularly transfemoral amputees, to lower the energetic and cognitive load necessary to walk and/or to perform other locomotion-related tasks, such as "climbing stairs", standing up, and so on.

The aid device according to the invention increases amputee's efficiency both under a metabolic and cognitive point of view, thanks to the combination of a prosthesis with an orthosis and to the operative connection between them and to their joint control. In particular, such connection and control, through passive or active (i.e. powering) components can allow a load transfer between the prosthesis and the orthosis and/or a coordinated movement of the two.

BRIEF DESCRIPTION OF THE DRAWINGS

In the following, reference will be made to the figures of the annexed drawings, wherein:

FIG. 1 shows a schematic perspective representation of an aid device according to a preferred embodiment of the invention;

FIG. 2 shows a diagram illustrating the operation modes of a control unit of the device of FIG. 1;

DETAILED DESCRIPTION OF PREFERRED EMBODIMENTS OF THE INVENTION

Figure 3B:
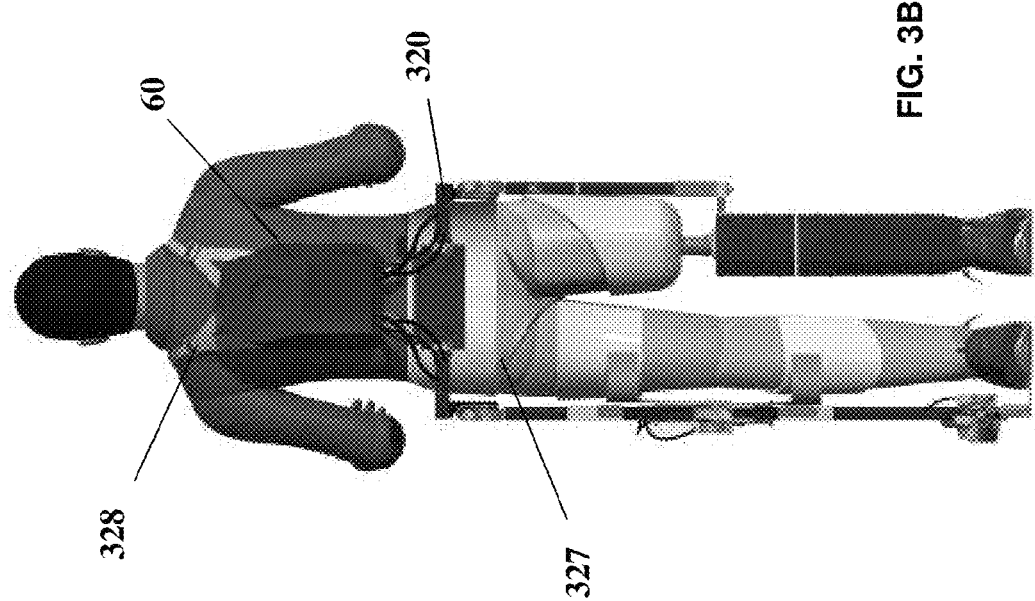
FIGS. 3A and 3B show a front and posterior view, respectively, of a specific implementation of the aid device of FIG. 1, wherein only a sub-group of the hardware components of this figure have been represented.

With reference initially to FIG. 1, it is shown an aid device 1 for the motor disabled according to a preferred embodiment of the invention which applies to transfemoral amputees.

Device 1 is conceived as an artificial cognitive system for the lower-limb functional replacement and assistance in daily living activities in transfemoral amputees.

Device 1 comprises a lower-limb prosthesis 2 for the amputated limb and an orthosis 3, the latter comprising a limb orthotic module 31 apt to be worn at the contralateral (sound) lower-limb and a pelvis module 32. Pelvis module 32 mechanically connects prosthesis 2 and limb orthotic module 31.

In the present example, both prosthesis 2 and limb orthotic module 31 have respective flexion/extension degrees of freedom at an ankle and at a knee portion thereof. The elements allowing such degrees of freedom are represented schematically in FIG. 1 and denoted by 51 and 52 for prosthesis's knee and ankle, respectively, and by 53 and 54 for knee and ankle of limb orthotic module 31, respectively. Preferably, the degrees of freedom of prosthesis 2 and of limb orthotic module 31 are active, i.e. powered, as explained in greater detail later on.

Moreover, also pelvis module 32 has at least one degree of freedom, in the present embodiment three degrees of freedom at each hip portion, in particular hip flexion/extension, hip intra-extra rotation and hip abduction/adduction. The elements allowing such degrees of freedom are represented schematically in FIG. 1 and denoted globally by 55. The degrees of freedom of pelvis module 32 allow the amputee to freely move his/her hips in space according to physiological movements. In the present embodiment, the degrees of freedom of the pelvis module in hip intra-extra rotation and hip abduction/adduction are passive, i.e. not powered, whereas hip flexion/extension is active, i.e. powered.

Prosthesis 2 and orthosis 3 represent mechatronic sub-systems of device 1.

Advantageously, device 1 also comprises passive components, preferably elastic components, allowing at least a partial load transfer from prosthesis 2 to limb orthotic module 31 and/or vice-versa during the execution of a motor task. Preferably, such passive components are arranged at pelvis module 32, in particular endowed in hip intra-extra rotation and abduction-adduction joints.

In the present example, when prosthetic leg 2 is in the stance phase, the weight of limb orthotic module 31 is partially unloaded onto ground, through pelvis module 32, by a foot 21 of prosthesis 2, and vice versa when the limb orthotic module 31 is in the stance phase. Limb orthotic module 31 touches the ground through a flexible plate-like mechanism 310 parallel to the amputee's foot.

Device 1 also comprises means for supplying external energy to prosthesis 2 and to limb orthosis 31. In a variant embodiment, pelvis module 32 can be energized as well, in combination or in alternative with energization of limb module 31 and/or of prosthesis 2.

In the present example, device 1 includes an on-board energizing unit 6 arranged at pelvis module 32, as shown schematically in FIG. 1. As mentioned above, in the present embodiment energizing unit 6 is apt to provide full or auxiliary power at the aforementioned degrees of freedom of prosthesis 2 and limb orthotic module 31. Energizing unit 6 may be implemented by a battery pack.

Device 1 also comprises a sensory system, preferably comprising multi-modal sensors. Preferably, such sensory system allows monitoring one or more of the following:
    prosthesis and/or orthosis status—in particular, active and passive joints are equipped with position and torque sensors;
    amputee's body motion and/or status—in particular, inertial measurement units (IMUS) are placed on the upper part of the patient body, preferably at pelvis module 32, to monitor torso and upper-limb posture/orientation, angular velocities and accelerations;
    interaction between subject and device 1—in this respect, orthosis 3 may have shells covered with distributed pressure sensors, which provide an estimate of the patient-device interaction force;
    interaction between prosthesis 2 and/or limb orthotic module 31 with the ground—in this respect, prosthesis foot 21 and amputee's foot are equipped with a respective sensorized foot insole, which preferably provides an estimate of the vertical ground reaction and the coordinates (on the foot surface) of the centre of pressure (CoP).

Generally speaking, the sensory system may comprise sensors for monitoring one or more of the following: linear and/or angular position of part(s) of device 1 and/or of the subject; forces and/or pressure and/or moments at part(s) of device 1, at the ground and/or between subject and device 1; speed and/or acceleration of part(s) of device 1 and/or of the subject.

Preferably, the sensory system is distributed over device 1 and comprises wireless sensors. By way of example, a few sensors are shown in FIGS. 1 and 2 and one of them is denoted by 7.

Device 1 also comprises a control unit 8 in communication with prosthesis 2, orthosis 3, energizing unit 6 and the sensory system. Preferably, communication between control unit 8 and the aforementioned sensors and/or the other components of device 1 is obtained by a wireless network.

Control unit 8 is shown also in FIG. 2 and denoted as "cognitive control unit".

Preferably, also control unit 8, or at least computational means thereof, is arranged at pelvis module 32, as shown schematically in FIG. 1.

Operation modes of control unit 8 and the associated data flow with the other components of device 1 are shown, by way of example, in FIG. 2.

As shown in said Figure, device 1 closes the loop with the amputee by means of an efferent feedback unit 81, preferably comprising vibro-tactile modules embedded in the human-robot physical interfaces. The latter provide the amputee with a feedback on robot, user-robot interaction and ground interaction status. In the example of FIG. 1, one of such vibro-tactile units is shown arranged at the prosthesis stump and denoted by 9.

Control unit 8 processes all data from the device sensory system and preferably give as output an estimation of one or more of the following:
a) the "amputee motor intention", which means to identify which locomotion-related task (e.g. walking, stairs climbing), or which motor transient (e.g. start and stop walking, sit-to-stand, or stand-to-sit) the amputee wants to perform, as well as close-to-real-time high level parameters characterizing this intention (e.g. gait cadence, etc.);
b) a "prevision of the risk of fall"; which means that the fusion algorithm will be able to timely address questions such as: "Is the subject close to fall down?", "Is the subject stumbling?";
c) an "evaluation of the amputee psychophysiological stress level", which means that the control system can evaluate the level of effort of the user to accomplish a certain motor task; we should imagine this output as an index which correlates to the amputee (physical and mental) effort;
d) the identification of the current "device-amputee system status": control unit 8 recognizes specific states like gait states (e.g. hell strike or toe-off) or posture states (e.g. weight transfer from prosthesis to orthosis).

Outputs a) to c) enter as inputs in a motor-primitive based control system of prosthesis and orthosis. More specifically, the "amputee motor intention" is used to select which motor primitive will be run for controlling the prosthesis, orthosis is and their dynamical coupling. The "prevision of the risk of fall" is used for fast modification of motor primitive parameters to initiate counter-measures to the detected fall. Finally, "the evaluation of the amputee psychophysiological stress level" is used to change motor-primitives parameters to provide the amputee with higher motion assistance and smoothly bring the amputee on a less-tiring steady-state condition. Being the selected motor primitive running, prosthesis and orthosis joints are preferably driven through an impedance control strategy. For the orthosis an alternative 'zero-impedance joint torque control' strategy is available. This mode is used to provide assistive torque with minimum output impedance, when needed. Last, but not least, output d) of the multi-sensory fusion algorithm, the "amputee-device system status", enters the efferent feedback unit block. In the present embodiment, as said above the status is encoded in a vibro-tactile temporally-discrete stimulation of a functional site of the amputee (e.g. the amputee's stump).

Therefore, control unit 8 of aid device 1 is based upon motor primitives as fundamental buildings block, thus endowing the device with semiautonomous behaviour for planning the motion of the prosthesis joints and the assistive action of the orthosis module. The device is capable of high-level cognitive skills, interfaced to the amputee through a bi-directional interaction.

Moreover, control unit 8 evaluate possible amputee's psychophysiological stress condition and on-line adapt the assistance strategy, as well as the gait pattern. Control unit 8 also provides the user with an augmented efferent feedback on the amputee-device status, thus promoting the emergence of a sense of body-ownership (cognitive efficiency).

Figure 3A:
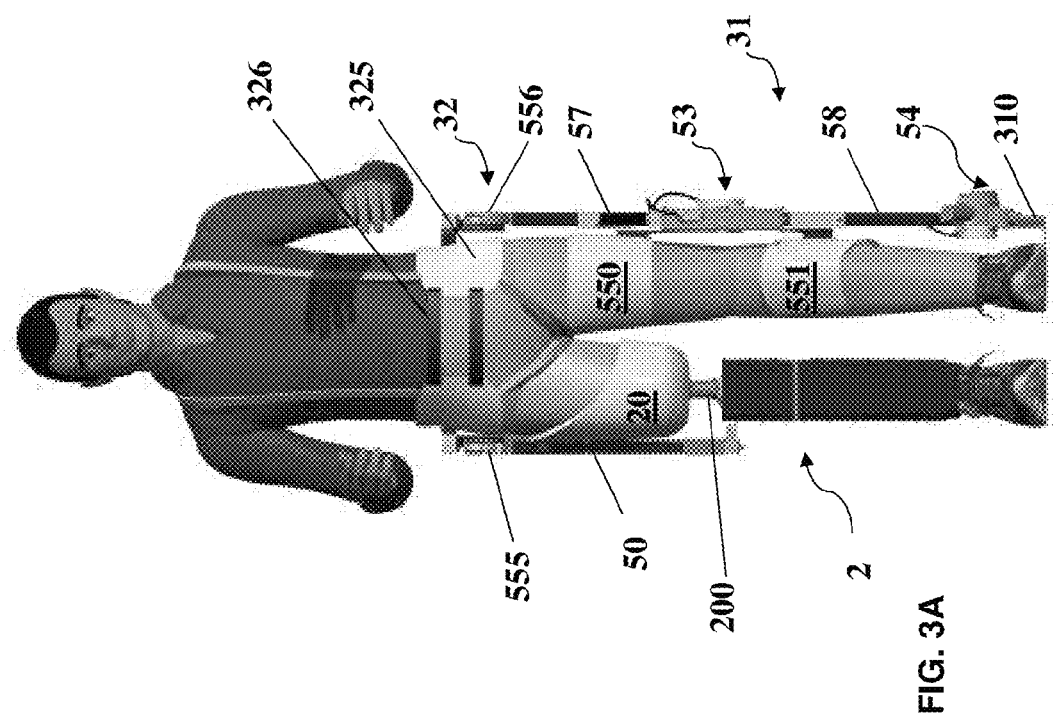

Some of the components introduced so far are shown in further detail in FIGS. 3A and 3B.

The specific implementation of device 1 shown in FIGS. 3A and 3B comprises prosthesis 2 with two active degrees of freedom, pelvis module 32 with two active degrees of freedom for the assistance of flexion-extension at each hip, and limb orthotic module 31—namely a knee-ankle-foot orthosis—with two active degrees of freedom for assisting flexion-extension of the knee and ankle is joints of the sound limb.

Prosthesis 2 is connected to pelvis module 32 by means of a passive mechanical coupling which will be detailed later on.

Prosthesis 2 is also connected to a thigh socket 20 by a standard tube 200 for prosthetics application.

Pelvis module 32 comprises a C-shaped frame 320 which houses—for each hip joint—a rotational actuator, in particular a motor, for assisting the hip flexion-extension. These two actuators are schematically represented in FIGS. 3A and 3B and denoted with 555 and 556, respectively.

As mentioned above, pelvis module 32 is also endowed with two passive degrees of freedom for each hip joint, namely intra-extra rotation and abduction-adduction. C-shaped frame 320 of pelvis module 32 also houses two passive joints for intra-extra rotation and abduction-adduction.

C-shaped frame 320 is also connected to tailored pelvis orthotic shells 325, fastened together by belts 326. Shells 325 and belts 326 allow the mechanical coupling of frame 320, and generally speaking of pelvis module 32, with the user pelvis.

For the amputated limb, hip flexion-extension actuator 555 transfers the assistive torque to the stump by means of a rigid bar 50 connected to prosthesis 2 by means of the aforementioned passive mechanical coupling. For the sound limb, hip flexion-extension actuator 556 transfers the assistive torque to the thigh by means of a rigid bar 57 connected to an orthotic cuff 550. Bar 57, which is parallel to the thigh of the sound limb, is then connected to knee-ankle-foot orthosis 31.

Knee-ankle-foot orthosis 31 comprises two rotational actuation units—denoted by 53 and 54 for consistency with FIG. 1—for the assistance of knee and ankle flexion-extension, respectively. These two rotational actuation units 53 and 54—based upon rotational motors—are coupled by a rigid bar link 58 that interfaces the shank of the sound limb by means of a further orthotic cuff 551. Finally, the ankle motor of unit 54 moves a rigid link which is mechanically is coupled to the shoe of the sound limb and which is denoted with 310 for consistency with FIG. 1.

In the example of FIGS. 3A and 3B, battery pack 6 and control unit 8 of device 1 are housed within a back pack 60 which is worn by the user by means of belts.

The weight of device 1 is partially transferred to the amputee's back by means of belts 328.

Finally, other belts 327, passing under the groin, avoid the system slipping upwards as a consequence of the interaction of device 1 with the terrain.

Of course, variant embodiments may provide different means for said lead transfer to the back and/or for avoiding said slipping.

Figure 4B:
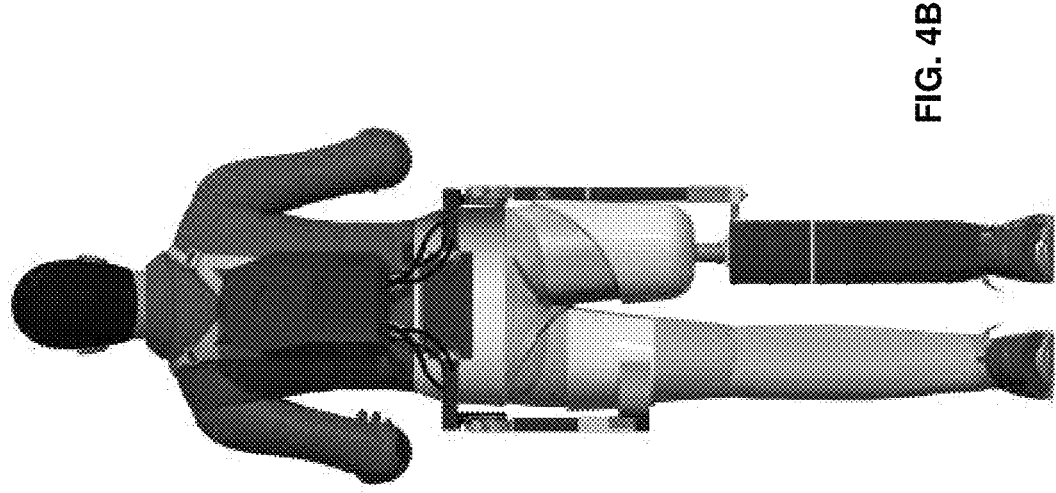
FIGS. 4A and 4B show a front and posterior view, respectively, of an aid device according to another preferred embodiment of the invention, wherein there have been represented the main hardware components.
Figure 4A:
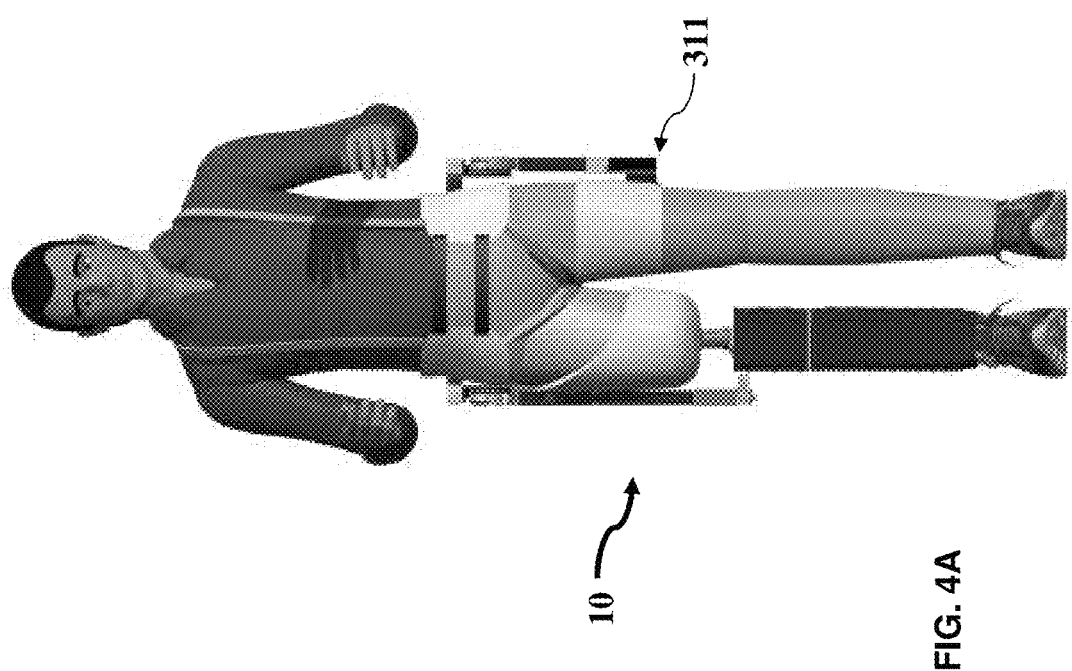

FIGS. 4A and 4B relate to a different embodiment of the device according to the invention, globally denoted by 10, wherein a thigh orthosis module 311 only is provided, i.e. the orthotic module does not extend to the knee and shank.

The remaining components, degrees of freedom and operation modes of device 10 can be the same as already described in conjunction with FIGS. 1 to 3B.

It will be appreciated that the aid device described above provides a multi-degree-of-freedom system with both lower-limb replacing and assistive capacities and allows the user to use the robotic aid on a whole-day basis.

It will be now better understood that the aid device of the invention, particularly in the embodiments described above, improves the amputee's efficiency under both a metabolic and a cognitive point of view.

As far as metabolic efficiency is concerned, the device allows decreasing the cardiovascular and muscular load on the amputee, to allow him/her to use the robotic aid on a whole-day basis. This is achieved through the presence of both the active transfemoral prosthesis, which pursues the functional replacement of the propulsion function of the amputated limb through active knee and ankle is joints, and the power-augmentation wearable orthotic device on the contralateral limb, which supports the "weak" sound leg in the hard task to compensate the efficiency deficit introduced by the active prosthesis.

As far as cognitive efficiency is concerned, thanks to the control unit and the feedback efferent unit, the device ensures the lowest cognitive load for the amputee. This is reached primarily by sharing the cognitive effort for the control between the user and the robot. The device behaves largely as a semi-autonomous, intelligent and bio-inspired pair of robotic legs, i.e. the prosthetic and the orthotic legs. The prosthetic leg functionally replaces the biological amputated leg. The orthotic device acts in parallel to the sound leg of the amputee. In both cases, a bio-inspired control approach based on motor primitives ensures the prosthetic leg to behave like a normal leg and the orthotic device to naturally co-operate with the sound limb, with very little need of conscious control from the user.

In particular, the device is able to infer the amputee's motor intention—and then to use it to control both prosthesis and orthosis—by processing the information coming from the human-robot interface. Such human-robot interface (connecting the movement intentions of the amputee with the actual motion of the robotic modules) relies on a complete monitoring of the movement of the user himself obtained through a pervasive, miniaturized, distributed sensing apparatus to monitor all the relevant kinematical and dynamical data from: the robot itself, the user's contralateral limb, hips and upper body; the device and amputee feet interaction with the ground; and the interaction forces at the physical interface between the amputee and the orthotic device. The motor intentions of the user are deduced—and then used to control the robot—from the movement of the rest of the body, therefore requiring the amputee to give little to none conscious effort to control the device and cooperate with it. The detected high-level motion intention is used to control the global functional task of the device (e.g. move forward, move backwards, stop, climb a stair step). Aside this command, the prosthesis behaves autonomously regarding the control of the single actuated joints.

By processing the information coming from the human-robot interface, the device is able to detect when the amputee is stumbling or is close to fall down. Having detected this risk, the device control system can help the amputee to execute the appropriate recovery action. Thanks to this skill, transfemoral amputees who will use the device are not frustrated by continuously thinking about walking and moving with the prosthesis.

By monitoring some physiological parameters, such as skin temperature, conductance and hearth-rate, the device is able to evaluate possible amputee psychophysiological stress condition. The idea is that if the device realizes that the amputee is under (physical or mental) stress, it can act on the control strategies by changing the type of assistance (e.g. increasing the amount of torque assistance) or the gait parameters (e.g. by reducing the gait cadence).

Finally, the device is able to provide the user with an augmented efferent feedback on the amputee-device status. Providing the amputee with a feedback on system status contributes to perceive the device as a part of his/her own body, i.e. to promote the sense of body-ownership. The efferent feedback contributes to reduce the amputee cognitive effort. Indeed, receiving a feedback from the technological aid on system status helps the amputee to increase his/her confidence in the device support, thus reducing his/her mental effort.

The invention provides also a method of allowing the execution of a motor task by a motor disabled, which method comprises the step of providing an aid device as described above.

The present invention has been described so far with reference to preferred embodiments. It is intended that there may be other embodiments which refer to the same inventive concept, that may fall within the scope of the appended claims.

BIBLIOGRAPHY

Datta D., Heller B., Howitt J. (2005). A comparative evaluation of oxygen consumption and gait pattern in amputees using Intelligent Prostheses and conventionally damped knee swing-phase control. *Clin Rehabil*, 19:398-403.

Dillingham T. R., Pezzin L. E., MacKenzie E. J. (2002). Limb amputation and limb deficiency: epidemiology and recent trends in the United States. *South Med J.*, 95(8): 875-883.

Ephraim P. L., Dillingham T. R., Sector M., Pezzin L. E., MacKenzie E. J. (2003). Epidemiology of limb loss and congenital limb deficiency: A review of the literature. *Archives of Physical Medicine and Rehabilitation*, 84(5): 747-761.

The Global Lower Extremity Amputation Study Group (2000). Epidemiology of lower extremity amputation in centres in Europe, North America and East Asia. *British Journal of Surgery*, 87:328-337.

Waters R. L., Perry J., Antonelli D., H. Hislop (1976). Energy cost of walking of amputees: the influence of level of amputation. *The Journal of Bone and Joint Surgery*, 58(1):42-46.

The invention claimed is:

1. An aid device for a motor disabled subject being a transfemoral amputee, comprising:
    a) a prosthesis for an amputated limb, the prosthesis comprising one or more actuator-controlled prosthesis joints each having one or more degrees of freedom;
    b) an orthosis configured to be worn at a limb contralateral to the amputated limb, the orthosis comprising one or more actuator-controlled orthosis joints, said prosthesis and said orthosis being operatively connected to each other;
    c) a wearable energizing unit to energize the prosthesis and the orthosis;
    d) a sensory system comprising a plurality of sensors configured for monitoring:
    d1) one or more of: linear position of one or more parts of the device, angular position of one or more parts of the device, linear position of the subject, angular position of the subject, forces at one or more parts of the device, pressure at one or more parts of the device, moments at one or more parts of the device, speed of one or more parts of the device, acceleration of one or more parts of the device, linear position of the subject, angular position of the subject, speed of the subject, or acceleration of the subject;
    d2) one or more of forces at ground, pressure at ground, or moment at ground, and
    d3) one or more of forces between the subject and the orthosis, pressure between the subject and the orthosis, or moments between the subject and the orthosis, and
    e) a processor-based control unit in communication with said prosthesis, said orthosis and said sensory system, wherein:
    said control unit is configured to jointly control said prosthesis and said orthosis to obtain a coordinated movement of said prosthesis and said orthosis and to obtain a load transfer between said prosthesis and said orthosis by
    i) processing data obtained from said sensory system,
    ii) based upon processed data, selecting coordinated motion commands for prosthesis and orthosis parts, and
    iii) implementing said motion commands to provide powered control, through said energizing unit, of said actuator-controlled prosthesis joints and said actuator-controlled orthosis joints.

2. The device according to claim 1, wherein said prosthesis is a lower-limb prosthesis and said orthosis comprises a lower-limb orthosis, the lower-limb orthosis being configured to extend, in use, at a sound limb thigh.

3. The device according to claim 2, wherein the lower-limb orthosis is configured to extend, in use, at the sound limb thigh and also at a sound limb shank.

4. The device according to claim 1, wherein said prosthesis and/or said orthosis have at least one flexion/extension degree of freedom.

5. The device according to claim 1, wherein said prosthesis is a lower-limb prosthesis and has a degree of freedom at an ankle and/or at a knee portion.

6. The device according to claim 1, wherein said orthosis comprises a lower-limb orthosis and has a degree of freedom at an ankle and/or at a knee portion.

7. The device according to claim 1, wherein said orthosis comprises a first limb orthotic module configured to be worn at a limb contralateral to the amputated limb and a second connection orthotic module mechanically connecting said first orthotic module to said prosthesis.

8. The device according to claim 7, wherein said energizing unit is arranged at said second orthotic module.

9. The device according to claim 7, wherein said second orthotic module has at least one degree of freedom.

10. The device according to claim 7, wherein said second orthotic module is configured to be arranged at the pelvis or back of an amputee and has at least one degree of freedom at each hip.

11. The device according to claim 10, wherein said second orthotic module has at least one flexion-extension powered degree of freedom.

12. The device according to claim 7, wherein said control unit is arranged at least partially at said second orthotic module.

13. The device according to claim 1, wherein said control unit is capable of outputting efferent feedback data to the subject wearing the device.

14. The device according to claim 13, comprising a vibro-tactile unit to provide said feedback.

15. The device according to claim 1, further comprising a motor in communication with said control unit, wherein said control unit is capable of implementing an impedance control strategy.

* * * * *